United States Patent
Sharma

(10) Patent No.: US 9,913,813 B2
(45) Date of Patent: Mar. 13, 2018

(54) OPTHALMIC TREATMENTS

(71) Applicant: Optosolve Research & Development Limited, Birmingham (GB)

(72) Inventor: Anant Sharma, Bedford (GB)

(73) Assignee: Optosolve Research & Development Limited (GB)

( * ) Notice: Subject to any disclaimer, the term of this patent is extended or adjusted under 35 U.S.C. 154(b) by 0 days.

(21) Appl. No.: 15/076,098

(22) Filed: Mar. 21, 2016

(65) Prior Publication Data

US 2016/0199320 A1    Jul. 14, 2016

Related U.S. Application Data

(62) Division of application No. 14/009,397, filed as application No. PCT/GB2012/000330 on Apr. 5, 2012.

(30) Foreign Application Priority Data

Apr. 5, 2011    (GB) .................................. 1105731.2
Apr. 5, 2011    (GB) .................................. 1105732.0

(51) Int. Cl.
  *A61K 31/135*    (2006.01)
  *A61K 31/137*    (2006.01)
  *A61K 9/06*    (2006.01)
  *A61K 9/08*    (2006.01)
  *A61K 31/4178*    (2006.01)
  *A61K 9/00*    (2006.01)
  *A61K 45/06*    (2006.01)

(52) U.S. Cl.
  CPC .......... *A61K 31/137* (2013.01); *A61K 9/0048* (2013.01); *A61K 9/06* (2013.01); *A61K 9/08* (2013.01); *A61K 31/135* (2013.01); *A61K 31/4178* (2013.01); *A61K 45/06* (2013.01)

(58) Field of Classification Search
  CPC combination set(s) only.
  See application file for complete search history.

(56) References Cited

U.S. PATENT DOCUMENTS 6,191,126 B1    2/2001    Gamache
  2002/0022663 A1    2/2002    Alfonso et al.

OTHER PUBLICATIONS

Dafny, et al., "5-HT and morphine interaction, effects on sensory input in caudate nucleus and substantia nigra.", Neuropharmacology. Sep. 1997;16(9):577-85.

Parhizkari, et al., "A stability-indicating HPLC method for the determination of benzalkonium chloride in 0.5% tramadol ophthalmic solution", Feb. 1995, vol. 40, Issue 3, pp. 155-158.

Ko, et al., "Analgesic effects of tramadol during panretinal photocoagulation.", Korean J Ophthalmol. Dec. 2009;23(4):273-6.

Potschka, et al.,"Anticonvulsant and proconvulsant effects of tramadol, its enantiomers and its M1 metabolite in the rat kindling model of epilepsy.", Br J Pharmacol. Sep. 2000;131(2):203-12.

Li, et al., "Clinical observation of tramadol on postoperative painment from LASEK". Yan Ke Xue Bao. Dec. 2005;21(4):114-5, 123.

Baudouin,et al., "Current treatments of xerophthalmia in Sjogren's syndrome", La Revue de Médecine Interne vol. 25, Issue 5, May 2004, pp. 376-382.

Van Santvliet , et al., "Determinants of eye drop size.", Surv Ophthalmol. Mar.-Apr. 2004;49(2):197-213.

Garlicki, et al.,"Effect of intraarticular tramadol administration in the rat model of knee joint inflammation.", Pharmacol Rep. Sep.-Oct. 2006;58(5):672-9.

Wenk,et al., "Effect of morphine sulphate eye drops on hyperalgesia in the rat cornea.", Pain. Oct. 2003;105(3):455-65.

Stiles,et al., "Effect of topical administration of 1% morphine sulfate solution on signs of pain and corneal wound healing in dogs.", Am J Vet Res. Jul. 2003;64(7):813-8.

Peyman, et al., "Effects of Morphine on Corneal Sensitivity and Epithelial Wound Healing: Implications for Topical Ophthalmic Analgesia", British Journal of Ophthalmology,1194; 78: pp. 138-141.

Kölln, et al., "mRNA expression of metabolic enzymes in human cornea, corneal cell lines, and hemicornea constructs.", J Ocul Pharmacol Ther. Jun. 2012;28(3):271-7.

Tarantini, et al.,"Peribulbar tramadol, clonidine, and ropivacaine in blind and seeing painful eyes.", Eur J Ophthalmol. Nov.-Dec. 2007;17(6):976-8.

Zöllner, et al.,"Topical fentanyl in a randomized, double-blind study in patients with corneal damage.", Clin J Pain. Oct. 2008;24(8):690-6.

*Primary Examiner* — Zohreh A Fay
(74) *Attorney, Agent, or Firm* — Forge IP, PLLC

(57) ABSTRACT

Aqueous compositions suitable for topical administration to the human or animal eye contain at least one water-soluble polymeric ophthalmic lubricant, such as hyaluronate, carbomer gel or hypromellose, together with a water-soluble analgesic. The analgesic may be an opiod, particularly an opioid having an affinity for 5-HT receptors, such as tramadol. The aqueous compositions may for example be used as artificial tears, and as general ophthalmic lubricants for treating conditions such as dry eye or blepharitis. Further compositions combine ophthalmologicallyactive agents, such as pharmaceuticals, with opioids, such as tramadol in particular. These compositions may be used to treat the eye while reducing pain or discomfort that would normally be produced by administering these particular pharmaceuticals to the eye, and increasing the efficacy of the pharmaceuticals. Compositions are also disclosed, containing opioids with 5-HT receptor activity, which are of general use in alleviating pain in and around the eye.

15 Claims, No Drawings

OPTHALMIC TREATMENTS

FIELD OF THE INVENTION

The present invention relates to the field of treatments for conditions of the human or animal eye. More particularly but not exclusively, it relates to products and methods for reduction of pain, discomfort, inflammation and the like, in and around the human and animal eye. It further relates to products and methods for alleviating the problem of an eye lacking in natural lubrication.

BACKGROUND OF THE INVENTION

The search for improved pain-killing or pain-management agents with fewer drawbacks and side-effects is perennial, and despite recent advances in pharmacology, there are still situations in which no fully satisfactory approach is yet known.

Natural opiates, such as codeine and in particular morphine, have been used as pain-killers for thousands of years. However, to be effective, they must generally be ingested, inhaled or (more recently) injected into the bloodstream. They thus tend to operate throughout the body, rather than it being possible to localise their effect. Additionally, the opiates tend to have side-effects on brain chemistry; the narcotic, perception-modifying and addictive properties of morphine and related compounds are notorious. Lethal doses can also be dangerously close to effective doses. Opiates tend therefore to be restricted to essential uses only, where their effectiveness outweighs their drawbacks.

Opioids are a broader class of compounds. Opioids include the naturally-occurring opiates, as well as semi-synthetic compounds made by chemical modification of opiates (e.g. hydromorphone, oxycodone, and buprenorphine); fully synthetic compounds (e.g. fentanyl, pethidine and methadone); and by some classifications, endogenous naturally-generated body chemicals such as endorphins. The fully-synthetic opioids include compounds having a high degree of structural similarity to natural opiates, as well as compounds that have different structural "backbones", but which nevertheless appear to operate in conjunction with similar receptors and/or have a similar mode of action to opiates.

Except in a few limited circumstances, opioids have not found widespread use when topically applied, or against less severe levels of pain.

A part of the human or animal body with specific problems in respect of pain management is the eye. Whether for physiological reasons (the eye has a far greater density of nerve fibres than skin), psychological reasons or both, the eye is usually a peculiarly sensitive area. The tissues of the eye also tend to have a structure not found elsewhere in the body. For example, the epithelial cells on the surface of the cornea tend to have a flattened profile, compared to corresponding cells of the outer layers of the skin, and they are also non-keratinising, i.e. they do not generate the keratin filaments that strengthen the outer layer of the skin.

There are also specific problems associated with the eye, a major issue being that many of the pharmaceuticals used in the treatment of eye conditions tend to cause at least irritation of the eye and its surrounds, and often distinct pain (while for many patients pain tolerances in and around the eye are in any case to be low).

The human eye, like the eyes of most terrestrial vertebrate animals, requires considerable lubrication and hydration in order to allow smooth movement of the eye within its socket and of the eyelid across the eye, and to maintain clarity of vision. This is generally achieved by the secretion of tears from glands adjacent the eye. Tears also help to keep the eye clear of foreign bodies and irritant materials, since these usually cause an increased flow of tears, which in conjunction with increased rates of blinking, helps to wash away the cause of the irritation.

One eye condition of particular concern is "dry-eye" (also referred to xerophthalmia or keratoconjunctivitis sicca) in which insufficient tears are produced to lubricate and hydrate the eye, eyelids and eye socket fully and/or tear production cannot increase in the normal manner in response to irritation of the eye. A related, more common problem is "dry-eye syndrome", also known as keratoconjunctivitis sicca, a condition in which the eyes do not make enough tears, or the tears evaporate too quickly. This may produce anything from mild discomfort to significant levels of pain, sufficient to affect a sufferer's day to day life.

Another eye condition of concern is blepharitis. Blepharitis is a condition in which the rims of the eyelids become inflamed (red and swollen) which can result in symptoms such as: burning, soreness or stinging in the eyes; crusty lashes; and/or itchy eyelids. Meibomitis or meibomian gland dysfunction is a form of blepharitis. Dysfunction and inflammation of the sebaceous glands on the margins of the eyelids (the meibomian glands) causes a reduced production of the oily substances (e.g. lipids) needed to keep the eye lubricated. The substance that is produced is more viscous and less effective at lubricating the eye.

In such conditions in which the lubrication of the eye is reduced, a frequent complication is that vision becomes blurred.

It is known to use lubricating compositions, such as "artificial tears", dilute solutions of water soluble polymers (such as sodium hyaluronate, hypromellose and/or carbomer gel) that substitute for the missing natural tears. These will temporarily ease the motion of the eye and improve clarity of vision. However, they do not reduce pain levels in the eye to a significant extent.

If conventional painkillers are administered to reduce pain in the eye, this can yield the unfortunate consequence that any lessening of discomfort leads to the blink rate of the eyelid falling. This reduces the generation of tears further, possibly worsening a "dry-eye" condition, probably retarding recovery from the condition, and making it more probable that adventitious foreign material could enter the eye without being flushed out, thus harming the eye further.

It would be desirable to be able to deal with all forms of localised pain or discomfort in and around the eye by locally-applied painkillers, for example in the form of eye-drops, ointments, gels, and so forth. However, commonly-used topical pain-killers such as NSAIDs (e.g. ibuprofen) appear not to have sufficient effect, while topically applied opiates appear not to have the efficacy of injected opiates. However, the side-effects of effective levels of injected opiates would probably be unacceptable.

U.S. Pat. No. 6,384,043 to Peyman discloses that certain opioids have an analgesic effect on a denuded eye (i.e. an eye in which the epithelial cells have been stripped away as part of a treatment, or have been locally penetrated in the case of an eye injury). However, this effect would appear to occur only where the epithelial layer of cells has been breached, this perhaps allowing penetration of this layer by the opiates. An alternative hypothesis is that this damage to the eye leads to the local appearance of opioid receptors, with which the topically-applied opioids may interact as a preliminary to blocking the transmission of pain signals along the nerves.

Whatever the mechanism involved, it has been found that topically-applied morphine has very little or no analgesic effect when applied to an undamaged eye. Possibly penetration is not occurring, or the necessary receptors are not appearing, or both.

It would hence be of benefit if a topically-applicable analgesic formulation could be devised that would be effective on the eye, whether the eye is damaged or not, particularly in order to reduce pain induced by otherwise satisfactory treatments applied to the eye, or to reduce pain in eye infections and conditions in general.

SUMMARY OF THE INVENTION

It is hence an object of the present invention to provide compounds and compositions that obviate some or all of the above problems and provide some or all of the above benefits.

According to a first aspect of the present invention, there is provided an aqueous composition topically administrable to a human or animal eye, comprising an aqueous solution of at least one water-soluble polymeric ophthalmic lubricating medium and an effective amount of at least one water-soluble analgesic composition.

Preferably, said aqueous composition comprises an artificial tears composition, applicable to the eye in drops form.

Advantageously, said water-soluble polymeric ophthalmic lubricating medium comprises a water-soluble polymer bearing a plurality of ionic or non-ionic polar groups, such as hydroxyl groups, amino groups, carboxylic acid groups and salts thereof.

Said polymeric ophthalmic lubricating medium may comprise sodium hyaluronate.

Said polymeric ophthalmic lubricating medium may comprise hypromellose (also known as hydroxypropyl methyl cellulose or HPMC).

Said polymeric ophthalmic lubricating medium may comprise carbomer gel.

The polymeric ophthalmic lubricating medium may comprise one or more alternative demulcents or mucoprotective agents.

Said demulcents may comprise one or more cellulose derivatives, such as carboxymethyl cellulose or hydroxypropyl methyl cellulose.

Said demulcents may comprise glycerol.

Said demulcents may comprise a dextran, optionally dextran-70 (a dextran having a molecular weight of around 70,000).

The aqueous composition may comprise a polyol as defined herein.

Said polyol may comprise a sugar, a sugar alcohol, a sugar acid or an uronic acid.

Said sugar alcohol may comprise sorbitol and/or mannitol.

Said polyol may comprise sorbitol, mannitol, glycerol or propylene glycol.

The polyol may comprise polyvinyl alcohol and/or polyethylene glycol.

The aqueous composition may comprise a combination of polyols, optionally glycerol and sorbitol or glycerol and propylene glycol.

The aqueous composition may comprise a polycarboxylic acid or salt thereof, optionally a carbomer.

The aqueous composition may comprise one or more lipids.

Said lipids may comprise phospholipids.

The aqueous composition may comprise at least one surfactant compound adapted to reduce the surface tension of the composition.

The aqueous composition may comprise a viscosity modifier.

Preferably, the aqueous composition has a viscosity of between 1 and 20 centipoise.

Advantageously, the aqueous composition has a viscosity of at least 2 centipoise, optionally at least 5 centipoise.

Preferably, the aqueous composition has a pH of at least 6.5.

Advantageously, the aqueous composition has a pH of up to 8.0.

The aqueous composition may have a pH in or near the range of pH 6.8 to pH 7.8.

Preferably, the aqueous composition has an osmolality in the range of about 200 to 400 milliosmoles per kilogram of water.

Advantageously, said osmolality is in the range of 250 to 350 milliosmoles per kilogram of water.

In a first embodiment, said analgesic composition comprises an opioid compound.

Said opioid compound may comprise a natural opiate.

Said opioid compound may comprise an opioid having an affinity for 5-HT receptors.

Said opioid having an affinity for 5-HT receptors may comprise tramadol or a derivative thereof.

The aqueous composition may comprise at least 0.01% and up to 2% w/v tramadol.

Optionally, the aqueous composition comprises at least 0.1% w/v tramadol.

The aqueous composition may comprise between 0.25% and 1.25% w/v tramadol.

In a second embodiment, said analgesic composition comprises a steroidal anti-inflammatory compound.

In a third embodiment, said analgesic composition comprises a non-steroidal anti-inflammatory compound (NSAID).

Said NSAID may comprise at least one compound selected from ibuprofen, ketorolac, nepafenac, bromfenac, suprofen, flurbiprofen, indomethacin, diclofenac, paracetamol and acetylsalicylic acid (aspirin).

In a fourth embodiment, said analgesic composition may comprise a local anaesthetic composition.

Said local anaesthetic composition may comprise a local anaesthetic compound selected from the amide group.

Said local anaesthetic compound may then comprise lignocaine.

Said local anaesthetic composition may alternatively or additionally comprise a local anaesthetic compound selected from the ester group.

Said local anaesthetic compound may then comprise tetracaine.

The analgesic composition may comprise GABAergic, noradrenergic or serotonergic compounds.

The analgesic composition may comprise gabapentin.

The analgesic composition may comprise a muscle relaxant agent, optionally baclofen.

The analgesic composition may comprise ketamine.

The analgesic composition may comprise amitryptiline.

The analgesic composition may comprise clonidine.

The analgesic composition may comprise capsaicin.

The analgesic composition may then comprise glyceryl trinitrate.

The analgesic composition may comprise a calcium channel blocker.

Said calcium channel blocker may comprise diltiazem, verapamil, nicardipine, flunarizine, cinnarizine or amlodipine.

The analgesic composition may comprise a topical anxiolytic.

Said anxiolytic may comprise a benzodiazepine, optionally diazepam, lorazepam, clonazepam, alprazolam or chlordiazepozide.

The aqueous composition may further comprise an antimicrobial agent, such as an antibiotic.

The aqueous composition may further comprise an anti-allergy agent, such as an anti-histamine, a cromoglicate and/or an anti-inflammatory agent.

Preferably, said aqueous composition is for use in the treatment of conditions involving deficiencies in natural tears in the eye.

Advantageously, said aqueous composition is for use in the treatment of dry-eye, as defined herein.

Preferably, said composition comprises a topically-applicable composition.

Said composition may comprise eye-drops, a cream, a gel, an ointment or the like.

Said composition may comprise a slow-release composition.

Said composition may comprise pellet means implantable in or adjacent the eye.

Said composition may be adapted to be injected in or adjacent the eye.

According to a second aspect of the present invention, there is provided a method for treating a condition involving deficiencies in natural tears in the human or animal eye, comprising the steps of substantially simultaneously administering to the eye an aqueous solution of at least one water-soluble polymeric ophthalmic lubricating medium and an aqueous solution of at least one water-soluble analgesic composition.

Preferably, the method comprises the administration to the eye of a single aqueous composition comprising both said at least one polymeric ophthalmic lubricating medium and said at least one water-soluble analgesic composition.

Advantageously, the method comprises the administration to the eye of an aqueous composition as described in the first aspect above.

According to a third aspect of the present invention, there is provided a composition for topical application in the treatment of an eye disorder or condition of the human or animal eye, comprising an ophthalmologically active substance adapted for the treatment of said disorder or condition or a symptom thereof, wherein the composition further comprises an opioid.

Preferably, said opioid comprises an opioid having an affinity for 5-HT receptors.

Advantageously, said opioid comprises tramadol or a derivative of tramadol.

In a preferred embodiment, said ophthalmologically active substance comprises a pharmaceutically-active agent that administered alone tends to cause pain, discomfort, inflammation, irritation or other undesirable sensations or reactions in or around the treated eye.

Advantageously, the ophthamologically active substance is selected from a group of pharmaceutically-active substances comprising aceclidine, acetazolamide, aciclovir, anecortave, apraclonidine, atropine, azapentacene, azelastine, bacitracin, befunolol, betamethasone, betaxolol, bimatoprost, brimonidine, brinzolamide, carbachol, carteolol, celecoxib, chloramphenicol, chlortetracycline, ciprofloxacin, cromoglycate, cromolyn, cyclopentolate, cyclosporin, dapiprazole, demecarium, dexamethasone, diclofenac, dichlorphenamide, dipivefrin, dorzolamide, echothiophate, emedastine, epinastine, epinephrine, erythromycin, ethoxzolamide, eucatropine, fludrocortisone, fluorometholone, flurbiprofen, fomivirsen, framycetin, ganciclovir, gatifloxacin, gentamycin, homatropine, hydrocortisone, idoxuridine. indomethacin, isoflurophate, ketorolac, ketotifen, latanoprost, levobetaxolol, levobunolol, levocabastine, levofloxacin, lodoxamide, loteprednol, medrysone, methazolamide, metipranolol, moxifloxacin, naphazoline, natamycin, nedocromil, neomycin, norfloxacin, ofloxacin, olopatadine, oxymetazoline, pemirolast, pegaptanib, phenylephrine, physostigmine, pilocarpine, pindolol, pirenoxine, polymyxin B, prednisolone, proparacaine, ranibizumab, rimexolone, scopolamine, sezolamide, squalamine, sulfacetamide, suprofen, tetracaine, tetracyclin, tetrahydrozoline, tetryzoline, timolol, tobramycin, travoprost, triamcinulone, trifluoromethazolamide, trifluridine, trimethoprim, tropicamide, unoprostone, vidarbine, xylometazoline, pharmaceutically acceptable salts thereof, and combinations thereof.

The ophthalmologically active substance may comprise an antioxidant or vitamin.

Said antioxidant may comprise vitamin A, vitamin C, vitamin E, lycopene, selenium, alpha-lipoic acid, coenzyme Q, glutathione, or a carotenoid.

The ophthalmologically active substance may comprise a metal complex.

The ophthalmologically active substance may comprise a non-steroidal anti-inflammatory drug (NSAID).

The ophthalmologically active substance may comprise is an antimicrobial agent.

The ophthalmologically active substance may comprise an antihistamine.

The ophthalmologically active substance may comprise proteins, antibodies or part of antibodies, deoxyribonucleic acid or ribonucleic acid.

Preferably, said composition comprises a topically-applicable composition.

Said composition may comprise eye-drops, a cream, a gel, an ointment or the like.

Said composition may comprise a slow-release composition.

Said composition may comprise pellet means implantable in or adjacent the eye.

Said composition may be adapted to be injected in or adjacent the eye.

According to a fourth aspect of the present invention, there is provided a method for treating an eye disorder or condition of the human or animal eye, comprising the steps of providing a composition comprising an ophthalmologically-active substance adapted for the treatment of said disorder or condition or a symptom thereof, together with an opioid, and administering said composition topically to the eye requiring treatment.

Preferably, said opioid comprises an opioid having an affinity for 5-HT receptors.

Advantageously, said opioid comprises tramadol or a derivative of tramadol.

The method may comprise the administration to the eye of a composition as described in the third aspect above.

According to a fifth aspect of the present invention, there is provided a composition comprising an opioid having affinity for 5-HT receptors for use in the treatment of pain associated with the human or animal eye.

Preferably, said opioid comprises tramadol or a derivative thereof.

Preferably, said composition comprises a topically-applicable composition.

Said composition may comprise eye-drops, a cream, a gel, an ointment or the like.

Said composition may comprise a slow-release composition.

Said composition may comprise pellet means implantable in or adjacent the eye.

Said composition may be adapted to be injected in or adjacent the eye.

The composition may be for use in the treatment of pain caused by administration of a pharmaceutically active substance to the eye.

The composition may then comprise both said opioid and said pharmaceutically active substance.

In a preferred embodiment, said composition is for use in the treatment of pain associated with medical conditions of the human or animal eye.

Said medical conditions may comprise dry-eye or dry-eye syndrome.

Said composition may then comprise an artificial tears composition comprising said opioid.

Said opioid may comprise tramadol or a derivative thereof.

Said composition may additionally or alternatively be for use in the treatment of blepharitis.

Said composition may additionally or alternatively be for use in the treatment of allergic eye disease.

Said composition may additionally or alternatively be for use in the treatment of infections of the eye.

Said composition may additionally or alternatively be for use in the treatment of inflammation of the eye.

Said composition may additionally or alternatively be for use in the treatment of autoimmune diseases of the eye.

Said composition may additionally or alternatively be for use in the treatment of ocular surface diseases such as pterygium and pingeculae.

Said composition may additionally or alternatively be for use in the treatment of glaucoma.

Said composition may additionally or alternatively be for use in the treatment of age-related macular degeneration.

Said composition may additionally or alternatively be for use in the treatment of post-operative inflammation and discomfort.

Said composition may additionally or alternatively be for use in the treatment of diseases of the lacrimal gland, conjunctiva, orbit and/or eyelid.

Said composition may additionally or alternatively be for use in the treatment of recurrent corneal abrasion, non-healing ulcers or persistent epithelial defects.

Said composition may additionally or alternatively be for use in the treatment of migraine and in particular ocular migraine.

Said composition may in an alternative embodiment be for use in the treatment of pain associated with surgical treatment of, or traumatic damage to, the human or animal eye.

The compositions of this aspect of the present invention may also be of use in the treatment of diseases and conditions of the eye not involving pain and/or discomfort, at least including the conditions and diseases disclosed above in cases in which there is no or minimal immediate pain or discomfort.

According to a sixth aspect of the present invention, there is provided a method of alleviating pain in or adjacent a human or animal eye, comprising the step of administering a composition comprising an opioid having affinity for 5-HT receptors to or adjacent a site of said pain.

Said method may comprise a method for treatment of dry-eye or dry-eye syndrome comprising the step of administering to the eye an artificial tears composition comprising said opioid.

Said method may alternatively comprise a treatment for any one of the diseases or conditions disclosed in the fifth aspect above.

Advantageously, said opioid comprises tramadol or a derivative thereof.

Said composition may comprise a composition as described in the fifth aspect above.

DETAILED DESCRIPTION OF THE INVENTION

Embodiments of the present invention will now be more particularly described by way of example.

In a first example, an eye was treated with pilocarpine drops to cause constriction of the pupil (in this particular example, as part of an ophthalmic diagnostic procedure, although pilocarpine is also be used therapeutically). Such drops can cause significant discomfort and excessive tear formation, possibly washing pilocarpine out of the eye before it could take effect. However, when drops containing tramadol were administered before or in conjunction with the pilocarpine drops, discomfort and tear formation were both greatly reduced. Effective constriction could also be produced with significantly lower levels of pilocarpine. Administered promptly after or in conjunction with tramadol administration, 0.5% w/v pilocarpine was found to be as effective as 1% w/v pilocarpine administered without tramadol present. This implies that the tramadol may well be improving the absorption of other drugs.

In a second example, a composition containing ciclosporin would normally be administered to the eye in post-operative treatment following a corneal transplant, to avoid transplant rejection. However, this would lead to significant additional levels of discomfort in the eye. Addition of 0.5% w/v tramadol to the composition would significantly reduce the discomfort, and should also improve the effectiveness of the ciclosporin.

In a third example, a conventional ophthalmic eye-drop formulation was made up, but with the addition of 0.5% w/v tramadol. This formulation was administered to the left eye of a healthy 47-year-old subject. Sensation in the left eye was noticeably reduced within 3 minutes of instillation of the tramadol formulation, and this numbing effect lasted for at least 110 minutes. Sensation in the right eye remained normal. No side-effects were noted.

In a fourth example, administration of the tramadol-containing eye-drop formulation of the third example to a patient suffering from "dry-eye" reduced the resultant discomfort as expected. However, this reduction of discomfort apparently led to a reduction in blinking, dryness remained and the physical signs did not improve. When a conventional "artificial tears" composition was applied instead, this composition containing a lubricating formulation comprising sodium hyaluronate, hypromellose and/or carbomer gel, the eye was better lubricated and physical signs improved. However, the discomfort remained, which for many patients would lead to actions such as rubbing the affected eye, counteracting much of the improvement. When 0.5% w/v tramadol was added to the lubricating "artificial tears" composition, however, and this combination was administered to the eye, pain and dryness were reduced simultaneously, and all symptoms and signs improved significantly more rapidly.

In a fifth example, a conventional "artificial tears" formulation was made up as a standard, containing an aqueous ophthalmic lubricating formulation comprising sodium hyaluronate, hypromellose and carbomer gel.

A new "artificial tears" formulation embodying the present invention was also made up, having substantially the same composition as the conventional formulation, above, with the addition of 0.5 mg tramadol per 100 ml of "artificial tears" (i.e. 0.5% w/v tramadol).

The conventional artificial tears formulation was administered to an eye of a patient suffering from dry-eye. This lubricated the eye, and some physical signs improved. However, the discomfort that had built up prior to this administration was not reduced.

When the new artificial tears formulation containing tramadol was administered to an eye of the patient suffering from dry-eye, not only was the eye successfully lubricated, promoting heating, but the discomfort was significantly lowered.

A wide range of additional or alternative components may be present in the "artificial tears" formulation, both to encourage its lubrication effect and for other purposes. Thus, demulcents (soothing agents) or mucoprotective agents may be included, which tend to form soothing and protective films over a surface such as that of the eye.

In "artificial tears", cellulose derivatives may be used for this purpose, such as CMC (carboxymethylcellulose) or HPMC (hydroxypropyl methyl cellulose, also known as hypromellose—see above). Glycerol is a low-molecular weight demulcent, while dextrans are high-molecular weight demulcents (dextran-70, a dextran having a molecular weight of around 70 kiloDaltons is believed to be particularly suitable). The choice of high or low molecular weight components probably depends on the viscosity requirements of the composition (for details, see below); the above cellulose derivatives will increase viscosity significantly, for example.

It is hypothesised that polyols in general would be beneficial components for such lubricating compositions. In the context of the present application, the term "polyol" should be understood to refer to any organic compound having at least two adjacent hydroxyl (—OH) groups, in which these —OH groups are not held in a trans conformation, relative to each other. Such polyols may have a linear, branched or cyclic structural backbone, and may be substituted or unsubstituted, as long as they are water-soluble and pharmaceutically acceptable. The term "polyol" thus includes short-chain molecules, including diols and triols, as well as longer-chain, higher molecular weight molecules with large or even indeterminate numbers of hydroxyl groups. Mixtures of polyols are equally possible.

Examples of suitable polyols include sugars, sugar alcohols, sugar acids and uronic acids. Preferred sugar alcohols include mannitol and sorbitol. Short-chain polyols such as glycerol or propylene glycol are also very useful in these formulations, glycerol being a particularly suitable component in this regard.

Mixtures of glycerol with other polyols, such as glycerol/sorbitol and glycerol/propylene glycol, are also found to be particularly useful.

To form a higher-viscosity or even slightly gelled composition, conventional viscosity modifiers such as cellulosics or even gelatin may be used, but it is not essential to use such high-molecular weight polymeric reagents. With polyols present, the addition of an additive such as a borate will result in a degree of loose cross-linking between hydroxyl groups on different molecules (the borate will tend to form labile complexes with the hydroxyl groups). Thus, the viscosity of the composition will rise, and can for example be controlled by regulating the precise level of borate added. This action will also depend on pH, so a system could be produced that would thicken or gel once administered, as its pH changed to that of its immediate environment in or adjacent the eye. Thus, a polyol such as glycerol may act both as a demulcent and as a viscosity regulator.

Emulsions and gels of various compounds may also be included.

Natural tears contain lipids, and analogous compounds may be used in artificial tears. Phospholipids, particularly anionic phospholipids may be included (both of the hydroxypropyl guar gel group and of the carbomer-based lipid gel group).

Surfactants, particularly non-ionic surfactants such as polysorbates, poloxamers and tetrafunctional block copolymers, may be used to lower the surface tension of the tear composition and thus enhance wetting of the surface of the eye; ionic surfactants may also be included.

Other water-soluble polymers that have successfully been incorporated into strtificial tears formulations include polyvinyl alcohol (PVA), polyethyleneglycol (PEG) and carbomers (which are mainly polyacrylate polymers—Carbopol® carbomers are a good example). Polyvinylpyrrolidone (PVP) has also been used with some success.

Some artificial tears formulations may contain hydrocarbons, such as white petrolatum, mineral oil and white soft paraffin, although such materials are in general more appropriate to corresponding eye lubricant ointment formulations.

It is usually desired for artificial tear compositions, such as those of the present invention, to have an enhanced viscosity or even to be slightly gelled. This increases the retention time of the liquid compositions in the eye and/or increases the comfort/soothing/cushioning effect experienced by the patient when the composition is administered to the dry, sore eye.

A viscosity of from about 1 to about 20 centiPoises is generally required, preferably from about 2 to 20 centiPoises and ideally in the range of about 5 to 20 centiPoises.

The artificial tears should also be formulated to have a pH and osmolality compatible with the eye. Thus, the compositions will have a pH in the range of about 6.8 to 7.8.

Alternatively, as mentioned above, the artificial tears could have a pH slightly outside this range, so that as the artificial tears change pH in use, towards that of the eye, their effective viscosity increases.

The desired osmolality of the compositions will generally be in the range of about 250 to 350 milliosmoles/kilogram water. This will usually be adjusted with sodium or potassium chloride, although if other salts such as borates are present (see above), these will also contribute.

The artificial tears compositions of the present invention may be applied topically to the cornea to relieve dry eye symptoms, whatever their cause. The compositions may equally be employed as ocular moisture drops, ocular comfort drops or ocular lubricants. In these cases, the drops would be conveniently applicable as one or two drops, either directly to the cornea or in the cul de sac of the eye. Lubricating ophthalmic ointments and creams may also be prepared, containing analgesics as described herein.

A wide range of alternative analgesics may be used in the artificial tears and other ophthalmic lubricants of the present invention.

NSAIDs, such as ibuprofen, ketorolac, nepafenac, bromfenac, suprofen, flurbiprofen, indomethacin, diclofenac, paracetamol and acetylsalicylic acid (aspirin), should be suitable.

Systems having GABAergic, noradrenergic and serotonergic properties should be particularly suitable. (GABAergic compounds affect biochemical processes involving gamma-amino butyric acid or GABA; similarly, noradrenergic compounds affect processes involving noradrenalin; and serotonergic compounds affect processes involving serotonin).

Gabapentin is an example of a useful analgesic in this context; in broad terms, it mimics GABA in many neurochemical processes.

Muscle relaxants such as baclofen are believed to be suitable analgesics for such artificial tears/ophthalmic lubricant compositions.

Other analgesics that should be effective include ketamine and amitryptiline.

Clonidine is a compound that reduces sympathetic outflow through the sympathetic nervous system and so should also be useful as an analgesic in such artificial tears/ophthalmic lubricant compositions.

Although capsaicin is best known as the active ingredient of chilli peppers and the like, when administered topically it can be used as an effective local anaesthetic (as long as it is not ingested). It may thus also be used in the artificial tears and other ophthalmic lubricants of the present invention.

Glyceryl trinitrate (GTN) has analgesic properties when administered at the correct levels; indeed, it may be combined with capsaicin in topical skin treatments to improve the effect of the capsaicin.

Another class of compounds that are likely to be effective as an analgesic in artificial tears/ophthalmic lubricant compositions of the present invention are calcium channel blockers. Examples of these include diltiazem, verapamil, nicardipine, flunarizine, cinnarizine and amlodipine.

It is also believed that anxiolytics, compounds for treating anxiety conditions, would be useful analgesic components in artificial tears/ophthalmic lubricant compositions of the present invention. Examples of anxiolytics which should be usable in topical compositions include the benzodiazepines, including diazepam, lorazepam, clonazepam, alprazolam and chlorodiazepoxide.

Where lubrication is low, and foreign bodies may not readily be washed out of the eye, damage to the surface of the eye or its surroundings is of concern. This may lead to subsequent infection. It may therefore be advisable to include an anti-microbial agent, typically an antibiotic, in the artificial tears/ophthalmic lubricant.

It may also be beneficial to administer an anti-allergy medication by including it in the artificial tears/ophthalmic lubricant; these anti-allergy medications include antihistamines, cromoglicates and anti-inflammatory agents (e.g. steroids).

If such analgesics are employed in artificial tears or other ophthalmic lubricating compositions, they should alleviate the pain and stress resulting from the lack of lubrication of the eye, while supplementing or even replacing natural tears; helping to soothe, wet and lubricate the eye, to avoid further harm to the cornea and other adjacent tissues; and to encourage healing (or at least to act as a palliative until natural healing is complete).

In a sixth example, an infection of the subject's eye required treatment with antibiotics. However, the subject was unable to open the respective eyelid due to the consequent pain. Administration of an eye-drop formulation comprising 0.5% w/v tramadol rapidly reduced the discomfort, permitting opening of the eyelid. This not only allowed administration of the antibiotics but also allowed reasonable vision in the treated eye, and appeared to help the resolution of the infection more rapidly than would have been expected.

In a seventh example, a 49 year old man presented with an allergic eye disease, resulting in significant prolonged itchiness. This itchiness improved within a few minutes after treatment with an eye-drop containing 0.5% w/v tramadol and the associated redness improved with time faster than for the conventional treatment with saline drops alone. Further experiments showed that an eye-drop containing 1.0% w/v tramadol produced even more rapid and effective results.

In an eighth example, a 49 year old man presented with dry eyes and unstable tear films, typical symptoms of "dry eye". The patient's tear osmolarity improved, after use of an eye-drop containing 0.5% w/v tramadol in one eye, from 312 milliOsmoles before instillation of the eye drop to 299 milliOsmoles one hour after instillation. The pain involved was also reduced. Use of an eye-drop containing 1.0% w/v tramadol reduced the patient's pain further.

In a ninth example, a middle-aged male with blepharitis and no corneal staining but a reduced tear break-up time was given eye-drops containing 1.0% w/v tramadol. The blepharitis improved, and so did the tear break-up time, along with improvement in irritable symptoms.

Topical administration of tramadol and other opioids with 5-HT receptor effects is likely to be beneficial in dry eyes, blepharitis, allergic eye disease, infections of the eye, inflammation of the eye, autoimmune disease of the eye, ocular surface diseases such as pterygium and pingeculae, glaucoma, age related macular degeneration and post-operative inflammation and discomfort. It is also likely to be beneficial in lachrymal gland, conjunctival, orbital and eyelid disease. Benefits are also expected in recurrent corneal abrasion, non-healing ulcers and persistent epithelial defects.

Administration of tramadol may also be of use in treating migraine, especially ocular migraine.

It is believed, on the basis of results to date, that treatment with tramadol and other opioids affecting the 5-HT receptor should be applicable as part of post-operative treatment following laser surgery, including PRK (photorefractive keratectomy). PTK (phototherapeutic keratectomy), LASIK (laser assisted in situ keratomileusis), LASEK (laser assisted in situ epithelial keratomileusis) and femtolaser surgery. Additionally, such treatment should alleviate pain and discomfort following injections of any kind into or around the eye.

As well as diseases causing discomfort or pain to the eye, such as dry eye and keratoconjunctivitis sicca, this treatment with tramadol should assist with recurrent pain syndromes such as recurrent corneal abrasion and non-healing ulcers. Tramadol treatment should also help in cases of chemical injury to the eye, as well as physical injury or insult thereto.

It is hypothesised that the particular effectiveness of tramadol and related compounds in this use may be because they interact not only with opioid receptors, but also with 5-HT receptors (also known as monoamine receptors), which mediate serotonin release. (Serotonin is also known as 5-hydroxytryptamine, hence 5-HT). Thus, there might be benefits from the serotonin released, which is associated for example with anxiolytic effects, and/or the interaction with the serotonin receptors might help to keep the tramadol localised near the site of pain.

A further distinction between the present invention and previous uses of opioids as analgesics is that opioids have generally only been considered for use in cases of severe pain, where their pain-killing effect outweighs their drawbacks. In the present invention, tramadol and its analogues have been found to be usable against lower levels of pain, without significant side-effects or other drawbacks.

What is claimed is:

1. A method for the treatment of alleviating pain associated with medical conditions of a human or animal eye, comprising topically administering, to a subject in need thereof, to or adjacent a site of said pain a composition comprising tramadol.

2. The method of claim 1, wherein the composition further comprises an aqueous solution of at least one water-soluble polymeric ophthalmic lubricating medium.

3. The method of claim 1, wherein the composition comprises between 0.01% and 2% w/v tramadol.

4. The method of claim 2, wherein the water-soluble polymeric ophthalmic lubricating medium comprises at least one compound selected from the group consisting of sodium hyaluronate, cellulose derivatives and carbomer gel.

5. The method of claim 1, wherein the composition comprises at least one surfactant species adapted to reduce surface tension of the aqueous composition.

6. The method of claim 1, wherein the composition comprises eye-drops, a cream, a gel, or an ointment.

7. The method of claim 1, wherein said method is for the treatment of pain caused by administration of a pharmaceutically active substance to the eye.

8. The method of claim 1, wherein said medical conditions are surgical treatment of a human or animal eye.

9. The method of claim 8, wherein said surgical treatment is being selected from the group consisting of post-operative inflammation and discomfort, for the treatment of pain following laser surgery, including PRK (photorefractive keratectomy), PTK (phototherapeutic keratectomy), LASIK (laser associated in situ keratomileusis) LASEK (laser assisted in situ epithelial keratomileusis) and femtolaser surgery.

10. The method of claim 1, wherein said medical conditions are deficiencies in natural tears in a human or animal eye.

11. The method of claim 10, wherein the composition further comprises an aqueous solution of at least one water-soluble polymeric ophthalmic lubricating medium.

12. The method of claim 10, wherein the composition comprises between 0.01% and 2% w/v tramadol.

13. The method of claim 11, wherein the water-soluble polymeric ophthalmic lubricating medium comprises at least one compound selected from the group consisting of sodium hyaluronate, cellulose derivatives and carbomer gel.

14. The method of claim 10, wherein the composition comprises at least one surfactant species adapted to reduce surface tension of the aqueous composition.

15. The method of claim 10, wherein the composition comprises eye-drops, a cream, a gel, or an ointment.

\* \* \* \* \*